United States Patent [19]

Cavitt

[11] 4,224,194
[45] Sep. 23, 1980

[54] PROCESS FOR PREPARING AN ETHYLENE OXIDE CATALYST

[75] Inventor: Stanley B. Cavitt, Austin, Tex.

[73] Assignee: Texaco Development Corp., White Plains, N.Y.

[21] Appl. No.: 15,509

[22] Filed: Feb. 26, 1979

[51] Int. Cl.$^2$ ............................................. B01J 23/50
[52] U.S. Cl. ................................ 252/476; 260/348.34
[58] Field of Search ................................ 252/463, 476

[56] References Cited

U.S. PATENT DOCUMENTS

| | | | |
|---|---|---|---|
| 3,962,136 | 6/1976 | Nielsen et al. | 252/463 X |
| 4,007,135 | 2/1977 | Hayden et al. | 252/476 X |
| 4,033,903 | 7/1977 | Maxwell | 252/476 |
| 4,066,575 | 1/1978 | Winnick | 252/476 X |
| 4,097,414 | 6/1978 | Cavitt | 252/463 X |

Primary Examiner—W. J. Shine
Attorney, Agent, or Firm—Carl G. Ries; Robert A. Kulason; Walter D. Hunter

[57] ABSTRACT

A process for preparing a modified, activated silver catalyst useful in the vapor phase epoxidation of ethylene with molecular oxygen is disclosed. The improved catalyst comprises an inorganic, porous support containing metallic silver and an effective amount of a higher alkali metal promoter which have been deposited coincidentally on the support.

The catalyst is prepared by impregnating a porous inorganic substrate with a solution comprising a silver compound such as a silver carboxylate, an organic amine solubilizing/reducing agent which also serves as a complexing agent for the silver compound, a perchlorate salt of a higher alkali metal, and an aqueous solvent. Optionally, the impregnating solution may contain at least one perhalogenated acid, such as perchloric acid. In a final step the impregnated support is heated at temperatures of from about 50° C. to about 300° C. to evaporate volatiles, decompose the silver compound to metallic silver and activate the catalyst.

26 Claims, No Drawings

PROCESS FOR PREPARING AN ETHYLENE OXIDE CATALYST

BACKGROUND OF THE INVENTION

1. Field of the Invention

The instant invention relates to a modified silver catalyst useful in the epoxidation of ethylene to ethylene oxide and more particularly to a silver catalyst promoted with at least one higher alkali metal which shows a greatly improved selectivity in the process for producing ethylene oxide by direct oxidation of ethylene with molecular oxygen.

2. Description of the Prior Art

Supported silver catalysts have long been used for the air oxidation of ethylene and more recently in a so-called "oxygen process". Although the first reference to the use of silver as such a catalyst was made by Walter in British Pat. No. 21,941 (1905), it was not until some thirty years later that the first disclosures were made of the use of silver as a catalyst in the vapor phase oxidation of ethylene to ethylene oxide. See Societe Francaise De Lefort, U.S. Pat. No. 1,998,878 (1935).

A variety of techniques have been developed for the depositing of relatively small, but highly active amounts of silver on surfaces of non-silver support such as alumina. For example, McKim and Cambron in *Canadian Journal of Research*, Volume 27, Section B (1949) at 813–827, describe a method for depositing particulate silver on a support by decomposing silver oxalate in aqueous ethanolamine at 60° C. and forming a paste which is applied to the surface of the support. In U.S. Pat. No. 3,043,854 issued July 10, 1962, to Endler, a silver coating formed by decomposition of a silver carbonate slurry is applied to a catalyst support surface.

It has been disclosed that supported silver catalysts can be prepared by impregnating a porous substrate with certain silver containing solutions and evaporating or decomposing the solutions to deposit silver on the substrate. U.S. Pat. No. 3,702,259 to Nielsen describes the use of an aqueous silver salt impregnating solution consisting essentially of a silver salt of carboxylic acid, an organic amine solubilizing/reducing agent such as ethylenediamine, a mixture of ethylenediamine or ethanolamine and ammonia or a mixture of ethylenediamine and ethanolamine. Van Bylandtlaan, in Belgium Pat. No. 808,278 (1974) employs an aqueous solution of hexamethylenetetramine with an ethylenediamine silver complex to deposit silver on an alumina support by decomposition. Additionally, it has been disclosed in Japanese Pat. No. 71/19,606 to Fujii et al that impregnation of inorganic supports with aqueous silver nitrate/alkanolamine complexes with subsequent thermal decomposition gives supported silver catalysts for ethylene epoxidation.

Recently it has been disclosed in British Pat. No. 1,413,251 to Nielsen and La Rochelle that certain alkali metals can be deposited on a refractory support coincidentally with the silver metal (U.S. Pat. No. 4,012,425).

Surprisingly, it has now been discovered that certain silver catalysts promoted with at least one higher alkali metal selected from the group consisting of cesium and rubidium are extremely stable, physically durable and highly selective in ethylene oxidation processes.

The promoted silver catalyst is easily prepared by impregnating a porous, inorganic substrate with a solution comprising:

(a) a silver compound,
(b) an organic amine solubilizing/reducing agent,
(c) a perchlorate salt of at least one higher alkali metal selected from the group consisting of cesium, rubidium and mixtures thereof sufficient to deposit on the said support an effective amount of the said higher alkali metal,
(d) an aqueous solvent and,
(e) a perhalogenated acid selected from the group consisting of perchloric acid, periodic acid and perbromic acid in an amount of from 0 to 20 gram milliequivalent weights per milliequivalent weight of the perchlorate salt in the said solution. The impregnated support is heated to decompose the silver compound thus depositing silver on the substrate and activating the catalyst.

It has been found that the instant promoted catalysts provide outstanding selectivity in air oxidation processes or oxygen processes using diluent materials such as nitrogen, carbon dioxide, steam, argon, methane or ethane. This is particularly important in that such processes are not closed systems and some proportion of the unreacted ethylene is lost by venting excess gas. Additionally, the instant catalysts show high attrition resistance and surprisingly high mechanical strength.

SUMMARY OF THE INVENTION

According to the broad aspect of the instant invention, the cesium or rubidium-modified silver catalysts of this invention are prepared by simultaneously depositing cesium or rubidium and the silver on a porous, inorganic support by impregnating the support with a liquid phase comprising a solution of:

(a) a silver compound,
(b) an organic amine solubilizing/reducing agent,
(c) a perchlorate salt of at least one higher alkali metal sufficient to deposit on the said support an effective amount of the said higher alkali metal,
(d) an aqueous solvent, and
(e) a perhalogenated acid selected from the group consisting of perchloric acid, periodic acid and perbromic acid in an amount of from 0 to about 20 milliequivalent weights per milliequivalent weight of the perchlorate salt in the said solution. When a perhalogenated acid is included in the impregnating solution, preferably, from about 0.5 to about 8 milliequivalent weights of the acid per milliequivalent weight of the perchlorate salt in the solution. Useful higher alkali metals include cesium, rubidium and mixtures thereof. The impregnated support is then heated at temperatures of from 50° C. to 300° C. to evaporate volatiles, decompose the silver compound to metallic silver, and activate the catalyst.

Organic amine solubilizing/reducing agents useful in the impregnating solution of this invention include:

(a) alicyclic diamines wherein at least one amino moiety is primary or secondary, but no more than one is primary;
(b) polyamines containing at least three amino moieties wherein at least one is primary or secondary; or
(c) amino ethers containing at least one ether linkage and at least one amino moiety which is primary or secondary.

DETAILED DESCRIPTION OF THE INVENTION

In accordance with a preferred embodiment, the supported, higher alkali metal promoted silver catalyst of the instant invention is prepared in four steps. In a first step, a solution comprising:

(a) a silver compound, (b) an organic amine solubilizing/reducing agent, (c) a perchlorate salt of at least one higher alkali metal sufficient to deposit on the said support an effective amount of the said higher alkali metal, (d) an aqueous solvent, and (e) a perhalogenated acid selected from the group consisting of perchloric acid, periodic acid and perbromic acid in an amount of from 0 to about 20 milliequivalent weights per milliequivalent weight of the perchlorate salt in the said solution is prepared, for example, by slurrying the silver compound such as a silver oxalate in water following which an amount of the organic amine solubilizing/reducing agent sufficent to dissolve the silver carboxylate is added. Finally, to the formed aqueous solution there is added a solution of cesium or rubidium perchlorate together with a perhalogenated acid, if desired, dissolved in an aqueous solvent which is preferably water.

In a second step, an inorganic porous support, as more fully described hereinafter, is impregnated by immersing the support in the impregnating solution at about atmospheric pressure and then subjecting the immersed support to vacuum at temperatures of from about 20° C. to about 40° C. After the vacuum is broken, the excess solution is drained. If desired, the vacuum impregnation step may be repeated. In the next step, the drained support is heated to evaporate volatiles at temperatures of from about 50° C. to 180° C. in a forced-air heater for a time from about 1 to about 12 hours. In a final step, the dried, impregnated support is heated in the presence of forced air at temperatures of from about 180° C. to about 300° C. to decompose the silver compound and activate the supported, promoted silver catalyst material.

The Impregnating Solution

The impregnating solution of the instant invention comprises:

(a) a silver compound, (b) an organic amine solubilizing/reducing agent, (c) a perchlorate salt of at least one higher alkali metal sufficient to deposit on the siad support an effective amount of the said higher alkali metal, (d) an aqueous solvent, and (e) a perhalogenated acid selected from the group consisting of perchloric acid, periodic acid and perbromic acid in an amount of from 0 to about 20 milliequivalent weights per milliequivalent weight of the perchlorate salt in the said solution. The impregnating solution can best be characterized as a homogeneous liquid at impregnating temperatures. The silver impregnating solution is formed by adding to a slurry of a silver salt in water at a temperature of about 0 to about 50° C. a solubilizing amount of certain organic amine solubilizing/reducing agents and finally adding, for example, an aqueous solution of a perchlorate salt of cesium or rubidium which, optionally, may contain a perhalogenated acid. Surprisingly, these silver impregnating solutions are stable in high solution concentrations at impregnating temperatures, and contain large amounts of silver which are carried to the support. This is due to the formation of a complex between the silver compound and the amine solubilizing/reducing agent. Additionally, these silver solutions are compatible with most cesium and rubidium as well as the perhalogenated acid salts and are of a viscosity which is suitable for impregnation of porous, inorganic supports.

Preferably, the silver compounds utilized in preparing the impregnating solutions of this invention are the silver carboxylates which readily thermally decompose. Such compounds can be carboxylates of mono-carboxylic or poly-carboxylic acids. Preferably, the silver salt is of a mono-carboxylic or di-carboxylic acid, wherein the organic moiety contains less than about 10 carbon atoms. Those carboxylates of less than about 10 carbon atoms are preferred in order to obtain a favorable concentration of silver in the organic acid salt, and ultimately thus in the complex solution, while providing for facile thermal decomposition. It should be noted that while silver salts of organic acids containing more than about 10 carbon atoms are useful, they produce a silver amine complex which becomes increasingly difficult to decompose as the molecular weight increases and will reduce the amount of silver ultimately available for deposition on the support.

Examples of suitable silver carboxylates include silver carbonate, silver acetate, silver malonate, silver glycolate, silver oxalate, silver formate, silver citrate, silver lactate, silver pyruvate, and the like. The most preferred silver carboxylates are silver oxalate and silver acetate because of availability and solubility.

The useful amine containing complexing agents of the instant invention can be generically described as:

(a) alicyclic diamines wherein at least one amino moiety is primary or secondary provided no more than one amino moiety is primary;

(b) polyamines containing at least three amino moieties wherein at least one is primary or secondary; and (c) amino ethers containing at least one ether (oxy) linkage wherein at least one amino moiety is primary or secondary.

Although all alicyclic diamines meeting the above criteria are useful as complexing agents, a preferred group of such diamines comprises piperazine, the N-alkyl substituted piperazines and the C-alkyl substituted piperazines.

While all aliphatic polyamines containing at least three amino moieties wherein at least one is primary are useful as complexing agents, a preferred group is the polyalkylene polyamines of the formula:

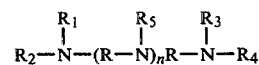

wherein R is a straight or branched chain alkylene radical having from 2 to about 4 carbon atoms, $R_1$, $R_2$, $R_3$, $R_4$ and $R_5$ are, independently, hydrogen or an alkyl radical of from 1 to 5 carbon atoms provided at least one of $R_1$, $R_2$, $R_3$, $R_4$ or $R_5$ is hydrogen; or $R_1$ and $R_2$ or $R_3$ and $R_4$ with the nitrogen to which they are attached to form a piperazine ring and n is an integer of from 1 to about 4. Examples include N(aminoethyl)-piperazine, N,N'-bis(2-aminoethyl)-piperazine, diethylenetriamine, N-methyldiethylenetriamine, triethylenetetramine, and the like. The most preferred polyalkylene polyamine compounds are diethylenetriamine and triethylenetetramine.

The amino ethers that are useful within the scope of the instant invention are the saturated and unsaturated, substituted and unsubstituted aliphatic amino ethers. These compounds may be straight or branched chain, acyclic, alicyclic, heterocyclic, or cyclic. Examples of such compounds include morpholine, the C-substituted morpholines, etc.; the bis(aminoalkyl) ethers, the N-alkyl bis(aminoalkyl) ethers, etc.; the polyoxyalkylene amines; the polyoxyalkylene polyamines, etc.; the alkoxyalkyl amines; amino-containing ethers derived from furan; and the like.

One preferred class of amino ethers is morpholine and the C-alkyl substituted morpholines. Another preferred class is the polyoxyalkyleneamines of molecular weight less than 1,000 and more preferably less than 500. Examples include the polyoxypropylenediamines of molecular weight less than about 400, and polyoxypropylenetriamine of molecular weight about 400. Both of the above polyoxypropyleneamine compounds contain terminal primary amino groups.

The amount of a particular amine utilized in preparing the silver impregnating solution is somewhat empirical. Generally that amount of amine solubilizing/reducing agent sufficient to completely dissolve the silver salts, i.e., a solubilizing amount, is utilized. This amount can be readily determined by the skilled artisan since the amount usually employed is sufficient to completely dissolve the required amount of silver salt can be determined by observation. An excess of the amine over that required to completely dissolve the silver salt can be employed, if desired. The amount of silver salt required is somewhat empirical and generally determined by the amount of silver ion required in solution and the porosity of the support.

As hereinbefore mentioned, it is desirable to have the complex as "rich" as possible in silver. Generally, the impregnating solution should contain an amount of about twice that desired in the finished catalyst on a weight percent basis with a support having a 50 percent porosity. It is preferable, therefore to utilize an impregnating solution which contains more than about 10 weight percent silver and, more preferably, from about 12 to about 25 weight percent silver.

When the preferred polyalkylene polyamines are utilized, it is desirable to have from about 1 to about 6 amine equivalents of the polyalkylene polyamine for each equivalent of silver in the impregnating solution.

The silver salt is preferably solubilized in the amine containing agent at temperatures in the range of about 20° C. to about 40° C. Temperatures in excess of 50° C. are not preferred, since high temperatures tend to cause accelerated decomposition of the complex.

Aqueous solvents useful in preparing the impregnating solutions of this invention include water, aqueous ammonia, and the like. In accordance with a preferred embodiment, water is utilized as the solvent. Water not only reduces the viscosity of the impregnating solution, reduces the amount of amine required to solubilize the silver salt, and reduces potential hazards of handling the solution, but also acts as an excellent solvent for the silver salt/amine complex formed by reaction of the silver salt and the amine, as well as the cesium or rubidium salt thus preventing premature precipitation.

Examples of suitable solubilizers include aqueous methylamine, ethylamine, diethylamine, triethylamine, and pyridine. It is, however, recognized that the marginal advantages of such solvents may be outweighed by the fact that certain lower molecular weight amines or ammonia can form explosive solids with silver. In addition, although not necessary, small amounts of hydrogen peroxide or other suitable oxidizing agents may be added to minimize premature reduction of the silver in the impregnating solution.

The impregnating solution may be prepared in a variety of ways. For example, the required amount of the perchlorate salt can be added directly to a solution comprising the silver salt, the amine solubilizing/reducing agent and the aqueous solvent. If desired, a perhalogenated acid selected from the group consisting of perchloric acid, periodic acid, perbromic acid and mixtures thereof in an amount which is preferably from about 0.5 to about 8 milliequivalent weights per milliequivalent weight of the perchlorate salt may be included in the impregnating solution. Where a free perhalogenated acid is employed in the impregnating solution, the preferred acid is perchloric acid.

Alternatively, the cesium or rubidium perchlorate can be prepared by mixing together in, for example, water, a soluble cesium or rubidium salt such as cesium or rubidium hydroxide, oxide or carbonate together with the stoichimetric requirement of perchloric acid needed to react with and convert the higher alkali metal salt to corresponding cesium or rubidium perchlorate. Preferably, an excess of the perchloric acid in an amount of from 0.5 to about 8 milliequivalent weights is added so that after the cesium or rubidium perchlorate is formed the resulting solution will contain free perchloric acid. The aqueous solution of the perchlorate salt together with excess perchloric acid, if utilized, is then added to the solution of the silver salt, the amine solubilizing/reducing agent and the solvent.

The amount of the cesium or rubidium perchlorate present in the impregnating solution will depend upon that amount desired in the activated catalyst, the solubility of the perchlorate salt, the porosity of the support, etc. Generally that amount of cesium salt sufficient to deposit from about $4 \times 10^{-5}$ gew to about $3 \times 10^{-3}$ gew cesium or rubidium per kilogram of finished catalyst is effective. Suitable impregnating solutions contain from about 10 ppm to about 800 ppm of the cesium or rubidium cation. The amount of cesium or rubidium cation required in solution is capable of determination by conventional analysis of the amount of material actually deposited. Generally, the impregnating solution should contain an amount about twice that desired in the finished catalyst on a ppm basis with a support having about 50 percent porosity.

The Support

The support utilized to form the novel promoted silver catalyst of the instant invention can be generally described as a porous, inorganic substrate having those characteristics which are well known in the art and particularly known in the ethylene epoxidation art. Suitable supports which can be used in accordance with the instant invention are glass, alumina, silica, silica-alumina, inert metals, silicon carbide and zirconia. It is essential that the support chosen have a high porosity (i.e., high solvent absorption), low surface area and a controlled pore size. Preferably, from about 70 percent to 100 percent of the pore diameters are between about 1 and 30$\mu$ and more preferably between about 1 and about 10$\mu$. The advantages of the instant catalyst are particularly evident when α-alumina supports are utilized.

A preferred support media has an average pore diameter of from about 4 to about 6$\mu$ with a pore volume of from about 0.3 to about 0.6 cc/g and has a surface area less than about 1 m$^2$/g. A particularly preferred support is high purity α-alumina having the above characteristics.

Preparation of the Supported Silver Catalyst

In preparing the stable, promoted silver catalyst of the instant invention, a suitable support is first contacted with the impregnating solution and subsequently heated at elevated temperature to first evaporate the volatiles and finally to decompose the silver carboxylate/amine complex and activate the catalyst material. Although the preparation of the supported catalyst can be accomplished in two steps, i.e., an immersion step and an evaporation, activating, and decomposition step at incrementally increasingly elevated temperatures, it is preferably to prepare the catalyst of the instant invention in the following steps.

After the impregnating solution has been prepared as described hereinabove, the substrate to be impregnated is contacted with the solution in a first step. This is preferably accomplished by immersion of the substrate in a suitably large body of impregnating solution to completely cover the substrate. The immersed substrate is then subjected to an evacuated atmosphere for a time period sufficient to remove entrapped air from the support pores at temperatures of from about 0° C. to about 50° C. and more preferably from about 20° C. to about 40° C.

The impregnation time will depend on the characteristics of the substrate and the viscosity of the impregnating solution and can be readily determined by the skilled artisan. Although somewhat empirical, it is generally sufficient to contact the porous substrate with the impregnating solution for a time from about five minutes to several hours. When utilizing impregnating solutions containing silver salts of polyalkylene polyamines, a time from about ten minutes to two hours is sufficient. After the substrate has been contacted for sufficient time under vacuum, the vacuum is broken to return the pressure to atmosphere and then the excess solution is physically drained from the substrate.

In a second stage the drained substrate is dried in the presence of a heated, flowing gas stream. The stream may comprise air or air diluted with sufficient inert gas to render the admixture substantially inert. The gas stream is heated to temperatures of from about 50° C. to 180° C. for a period sufficient to evaporate the volatiles. Generally, the time required to dry the impregnated substrate is somewhat empirical and can be readily determined by the skilled artisan for a particular substrate and impregnating solution. Time periods of from about one to about twelve hours have been found sufficient. It should be noted that, during the drying step, temperatures in excess of 180° C. should be avoided as the complex may tend to decompose too rapidly and/or cause the volatiles to evaporate so readily as to disturb the uniformity of the catalyst material. Although not required, it is found that first thoroughly drying the impregnated substrate prior to thermal decomposition yields a more uniform catalyst.

In a third step the dried impregnated substrate is heated in the presence of flowing air, or a flowing inert atmosphere to temperatures in excess of about 180° C. and preferably from about 180° C. to about 300° C. to decompose the silver salt and activate the catalyst. Although somewhat empirical generally times in the range from about one to twelve hours have been found sufficient.

It will be realized by the skilled artisan that depending on the particular solvent employed in preparing the impregnating solution the times required for drying may be somewhat variable. The specific times required are generally within the above broad limits and can be determined by the skilled artisan without undue experimentation. Additionally, when high molecular weight amines are utilized, washing of the dried substrate may be advantageous to remove excess organic material prior to activation. The washing may be accomplished in a conventional manner with lower alkanols.

Surprisingly, it has been found that the selectivity of the silver catalysts of this invention can be further improved by removing the outer surface or skin of the catalyst after the impregnated catalyst support has been heated at temperatures of about 180° C. to about 300° C. to evaporate the volatiles, convert the silver compound to silver metal and activate the catalyst. The reason for this increased activity after removal of the outer surface following the heating or silver salt reduction step is not fully understood. Removal of the outer surface of the catalyst can be carried out by any one of a number of methods well known in the art such as by tube milling, ball milling, sand blasting, etc. or by any other convenient method for abrading or wearing away the outer surface of the catalyst. The weight of the catalyst removed during this final activation operation if utilized, is small and generally will be from about 1 to about 10 weight percent and preferably from about 2 to about 6 weight percent based on the initial catalyst weight.

The Oxidation Reaction

The cesium or rubidium promoted silver catalysts of the instant invention have been shown to be particularly selective catalysts in the direct oxidation of ethylene with molecular oxygen to ethylene oxide. The epoxidation of ethylene to ethylene oxide can best be described as a controlled oxidation. It is important to minimize complete oxidation in accordance with the epoxidation process while maximizing the selectivity and conversion to the desired epoxidized products.

The conditions for carrying out such an oxidation reaction in the presence of silver catalyst generally and more particularly the novel, promoted catalyst of the instant invention are broadly described in the prior art. Such methods and manner of production are well known to the skilled artisan. For example, those methods which appear and are described in U.S. Pat. No. 3,119,837, British Pat. No. 1,314,613 and British Pat. No. 1,132,095. These teachings apply to a number of conditions including suitable temperatures, pressures, residence times, diluents, inhibitors and the like. Additionally, the desirability of recycling unreacted feed or use of successive conversion processes such as by employing series reactors, can be readily determined by the skilled artisan.

It has been found that the promoted silver catalyst of the instant invention is surprisingly stable under a broad spectrum of reaction conditions, while maintaining a high degree of selectivity and productivity.

Regardless of the character of the support utilized, the catalyst is preferably shaped into particles, pellets, spheres or the like of a suitable size for employment in fixed bed application. It will be realized that conventional commercial fixed bed ethylene oxidation reactors may be utilized. Such reactors typically take the form of a plurality of parallel elongated tubes packed with a catalyst material.

Generally, it has been found that the promoted catalyst of the instant invention is highly useful in both the so-called air oxidation or oxygen processes, wherein ballast "gases" are primarily comprised of nitrogen, carbon dioxide, steam, argon, helium, methane, ethane or other saturated hydrocarbons.

Generally, the process is carried out in vapor phase wherein a single gaseous feed stream is continuously charged to a suitable catalyst containing reactor. The reaction is carried out at temperatures from about 200° C. to about 300° C., and preferably in the range of about 220° C. to about 260° C. The pressures are not critical and may vary from about atmospheric to about 35 atm. with about 13 atm. to about 20 atm. being preferred at the preferred temperature range. The feed admixture is preferably fed in a single stream to the reactor in order that the constituents be thoroughly admixed.

The invention will be further illustrated by the following specific examples, which are given by way of illustration and not as limitations on the scope of this invention.

EXAMPLE I

This example illustrates preparation of the stable, supported silver catalyst of the instant invention. In a first step, silver oxalate was prepared. To a 4000 ml beaker equipped with a magnetic stirring bar there was added 199 g of ammonium oxalate and 1000 ml of deionized water following which the beaker contents were heated to about 60° C. with stirring. A solution of 454 g of silver nitrate in 1000 ml of dionized water was prepared with mixing at 60° C. in a 2000 ml beaker. The silver nitrate solution was then added slowly to the ammonium oxalate solution with stirring and the resulting slurry was stirred for an additional 15 minutes while cooling in air. In the next step the slurry was filtered through a Buchner funnel after which the precipitate, i.e., the silver oxalate, was washed first with 500 ml of hot, deionized water in small increments and then with 500 ml of cold, anhydrous methanol in small aliquots. After removing most of the liquid from the precipitate with vacuum suction, the moist cake was broken up and added slowly to 534 g of deionized water with stirring. The creamy, homogeneous, slurry thus-obtained was cooled to below room temperature with an ice bath while 400 g of diethylenetriamine was added with stirring while keeping the solution temperature at 40° C. or below.

After all solids had dissolved, the promoter solution containing cesium perchlorate and free perchloric acid was slowly added with stirring to yield the impregnating solution. Preparation of the promoter solution was accomplished by adding (1) 4.81 g of a perchloric acid solution formed from 5 g of 71 percent perchloric acid in 23.4 g of water; (2) 0.881 g of 50 percent aqueous cesium hydroxide solution; and (3) sufficient water to make 40 g and in a final step rinse water from the bottle containing the initial 40 g increment was added to form 53 g of the promoter solution. The promoter solution contained 0.68 g of cesium perchlorate (2.93 milliequivalents) and 0.30 g. of free perchloric acid (2.98 milliequivalents).

The above-described impregnating solution was utilized to impregnate a total of 2,223 g of a commercial alumina support (¼" spherical pellets) having a pore volume of 0.406 cc/g, a surface area of less than 1 m$^2$/g and an average pore diameter of about 5μ sold under the tradename the Norton Company's "Alundum", type LSA-05588. The amount of the impregnating solution remaining after the impregnation step was 202 g. During the impregnation the support and the solution in which the support was immersed were placed under vacuum and then the vacuum was released. This vacuum cycle was repeated after which the wet catalyst was drained, spread on two 14" by 16" trays and placed in a forced-air production oven preheated to 150° C. With the damper set at full open the catalyst was heated for 2 hours at 125°–130° C. Then the temperature was increased to 250° C. and maintained at that temperature for 1 hour with maximum air intake with exhaust 75 percent closed. The thus-treated catalyst was cooled to 50° C., then bottled and weighed. A total of 2,462 g of silvergray catalyst (Batch A) was recovered.

A second batch of catalyst weighing 2572 g. (Batch B) was prepared following the same procedure as described for Batch A. The support employed was the same as previously described. The amount of the impregnating solution remaining after impregnation of the catalyst was 208 g.

Catalyst Batches A and B were composited and placed inside a 5 gal. pail lined on the sides, bottom and closure with No. 100 sandpaper. The pail and contents were then rotated on a roller mill for 5 minutes in order to remove the outer surface of the catalyst pellets. After the abrading step had been completed the composite batch was removed from the pail and the dust present was removed by blowing with clean air. During the abrading operation about 1.8 percent of the initial catalyst weight was removed. A sample of this catalyst (Catalyst I) was submitted for silver and cesium analyses by atomic absorption.

Catalyst I was tested in a miniature ethylene oxide reactor employing 3.5 g of 30–40 mesh catalyst in a 0.2×5 inch reactor zone. The test was run at a reactor temperature of 245° C., mass velocity of about 1.5 g feed/g of catalyst/hour and a reactor pressure of 200 psig. The feed gas composition was 30 mole percent ethylene (99.8 minimum mole percent purity), 8 mole percent oxygen, 30 mole percent methane and the balance nitrogen. The performance results at an ethylene conversion of 13.2 percent are shown in Table 1. Ethylene dichloride inhibitor was added in amounts necessary to optimize the selectivity.

EXAMPLE II

An additional cesium-modified, silver catalyst (Catalyst II) was prepared and activated in the same manner as described in Example I. This catalyst was tested with the same gas composition in the same way and utilized the same support material as in Example I. Details relating to this catalyst are included in Table 1.

TABLE 1

| Catalyst | Ag (wt %) | Cs (ppm) | Perchlorate Concentration In Impregnating Solution | | Reaction Temperature (°C.) | ΔEO$_2$ (mole %) | Selectivity to Ethylene Oxide$_3$ (mole %) | Ethylene Conversion (%) |
|---|---|---|---|---|---|---|---|---|
| | | | CsClO$_4$ (meq)$_1$ | HClO$_4$ (meq)$_1$ | | | | |
| I | 9.3 | 131 | 0.22 | 0.22 | 245 | 3.26 | 82.5 | 13.2 |
| II | 9.5 | 94 | 0.22 | 0.22 | 248 | 3.36 | 82.1 | 13.4 |

TABLE 1-continued

| Catalyst | Ag (wt %) | Cs (ppm) | Perchlorate Concentration In Impregnating Solution | | Reaction Temperature (°C.) | $\Delta EO_2$ (mole %) | Selectivity to Ethylene Oxide[3] (mole %) | Ethylene Conversion (%) |
| --- | --- | --- | --- | --- | --- | --- | --- | --- |
| | | | $CsClO_4$ $(meq)_1$ | $HClO_4$ $(meq)_1$ | | | | |
| III | 9.1 | 99 | * | — | 254 | 3.30 | 79.9 | 13.6 |

*Cesium was added to catalyst as CsOH rather than CsClO₄ (Comparative example)
[1]meq = milliequivalent
[2]Ethylene oxide in reactor exit stream
[3]Based on oxygen converted

EXAMPLE III

In this comparative example a catalyst was prepared (Catalyst III) and tested in the same manner as in Example I with the exception that in the impregnating solution the cesium was present as cesium hydroxide. Tests results are shown in Table 1.

EXAMPLES IV AND V

Two additional cesium-modified, silver catalysts (Catalysts IV and V) were prepared and activated in the same manner as in Example I. In testing these catalysts the mass velocity of the gas entering the reactor was about 5 g of feed/g of catalyst per hour, and the reactor pressure was 200 psig and the inlet gas composition was 7 mole percent ethylene (99.8 minimum mole percent purity), 6 mole percent oxygen and the balance nitrogen. Test results are set out in Table 2.

EXAMPLE VI

In this comparative example a catalyst (Catalyst VI) was prepared and tested in the same manner as the catalysts of Examples IV and V with the exception that the catalyst support was impregnated with a solution containing cesium as cesium hydroxide. Test results for Catalyst VI are given in Table 2.

slurry was obtained. To the slurry chilled in an ice water bath there was slowly added with stirring, 120 g of diethylenetriamine while maintaining the solution temperature below 40° C. After all of the solids had dissolved, the solution was divided into four equal parts of 103 g each and to each part there was added 0.180 g, 0.360 g, 0.540 g, and 1.08 g respectively of perchloric acid solution which had been made up from 15 g of 71 percent perchloric acid and 70 g of deionized water. The four impregnating solutions were utilized to impregnate four 80 g lots of commercial alumina support sold under the tradename of the Norton Company's "Alundum" type LSA-05588. The wet catalyst was drained after two evacuations under the solution and placed on stainless steel trays for oven drying and activation. Next, the catalyst was dried at 125° C. for one hour with one pass air flow and then heated at 250° C. for one hour with oven exhaust 75 percent closed.

Samples of these four catalysts (Catalyst VII, VIII, IX and X) were submitted for silver and rubidium analyses by atomic absorption methods.

Using a miniature ethylene oxide reactor with 3.5 g of 30–40 mesh catalyst in a 0.2×5 inch reaction zone, three of the above-described catalysts (Catalysts VII, VIII and IX) were tested for selectivity. The mass velocity of the feed gas was about 2.5 g feed/g of catalyst/hour and

TABLE 2

| Catalyst | Ag (wt %) | Cs (ppm) | Percholate Concentration In Impregnating Solution | | Reactor Temperature (° C.) | Selectivity to Ethylene Oxide[2] (mole %) | Ethylene Conversion (%) |
| --- | --- | --- | --- | --- | --- | --- | --- |
| | | | $CsClO_4$ $(meq)_1$ | $HclO_4$ $(meq)_1$ | | | |
| II | 9.5 | 94 | 0.22 | 0.22 | 241 | 79.6 | 21.2 |
| IV | 9.3 | 95 | 0.22 | 0 | 243 | 79 | 21.6 |
| V | 9.3 | 244 | 0.44 | 0 | 280[3] | 72.5 | 16.3 |
| VI | 9.4 | 104 | * | — | 241 | 78.6 | 21.6 |

*Cesium was added to catalyst as CsOH rather than as CsClO₄ (Comparative example)
[1]meq - milliequivalent
[2]Based on ethylene converted
[3]Highest temperature obtainable with reactor A number of rubidium-promoted silver catalysts were prepared and tested in the same general manner as described for the cesium-promoted silver catalysts.

EXAMPLES VII-X

A slurry of silver oxalate was prepared by adding a hot solution of 135 g of silver nitrate in 500 cc of deionized water with stirring to a hot solution of 60 g ammonium oxalate in 500 cc of deionized water. After stirring for an additional period of about 20 min. the slurry was filtered through a Buchner funnel following which the silver oxalate was washed with 200 c of deionized water and finally with 200 cc of cold anhydrous methanol. While the silver oxalate was still damp, it was broken up and added to 160 cc of deionized water containing 0.163 g of rubidium perchlorate. The solids present were stirred into the water until a creamy homogeneous the reactor pressure was 200 psig. Composition of the feed gas was 30 mole percent methane, 30 mole percent ethylene and 8 mole percent oxygen with the balance being nitrogen. Details relating to these tests are given below in Table 3.

EXAMPLE XI

In this example a catalyst (Catalyst XI) was prepared and tested in the same manner as in Examples VII-IX with the exception that the impregnating solution contained cesium as cesium perchlorate and the solution contained free perchloric acid. Test results for this catalyst are also set out in Table 3.

The data in Table 1 show that with Catalyst I of this invention, the selectivity to ethylene oxide is about 2.6 mole percent greater than that obtained with Catalyst III where the catalyst support was impregnated with a solution containing cesium as cesium hydroxide. Likewise, it is shown by the data in Table 2 that a higher degree of selectivity was achieved with the catalysts of this invention than with the art catalyst (i.e., Catalyst VI) where the support was impregnated with cesium hydroxide rather than cesium perchlorate. In Table 3 the data indicate that a highly satisfactory catalyst can be prepared using rubidium as the alkali metal promoter.

TABLE 3

| Catalyst | Ag (wt %) | Cs (ppm) | Perchlorate Concentration in Impregnating Solution | | Reactor Temperature (°C.) | $EO^2$ (mole %) | Selectivity to Ethylene Oxide[3] (mole %) |
|---|---|---|---|---|---|---|---|
| | | | $RbClO_4$ (meq)[1] | $HClO_4$ (meq)[1] | | | |
| VII | 8.93 | 107 | 0.22 | 0.22 | 235 | 2.20 | 82.4 |
| VIII | 9.20 | 109 | 0.22 | 0.45 | 235 | 2.28 | 81.7 |
| IX | 9.56 | 114 | 0.22 | 0.67 | 235 | 2.20 | 82.3 |
| X | 9.27 | 111 | 0.22 | 1.35 | [4] | [4] | |
| XI | 9.25 | 131 | 0.22[5] | 0.22 | 235 | 2.55 | 83.1 |

[1] meq = milliequivalent
[2] Ethylene oxide in reactor exit stream
[3] Based on oxygen converted
[4] Catalyst X was not tested
[5] Milliequivalents of $CsClO_4$

What is claimed is:

1. A process for preparing an activated silver catalyst for the vapor phase epoxidation of ethylene with an oxygen-containing gas which comprises:
   contacting a porous, inorganic, catalyst support material with an impregnating solution; and,
   heating the impregnated support material at temperatures from about 50° C. to 300° C. to evaporate volatiles and activate said catalyst,
   wherein said impregnating solution comprises:
   (a) a silver salt,
   (b) an organic amine solubilizing/reducing agent,
   (c) a perchlorate salt of a higher alkali metal selected from the group consisting of cesium, rubidium and mixtures thereof sufficient to deposit on the said support an effective amount of the said higher alkali metal,
   (d) an aqueous solvent, and
   (e) a perhalogenated acid selected from the group consisting of perchloric acid, periodic acid, perbromic acid and mixtures thereof in an amount of from 0.5 to 20 milliequivalent weights per milliequivalent weight of the perchlorate salt in the said solution.

2. The process of claim 1 wherein the said organic amine solubilizing/reducing agent is selected from the group consisting of:
   (A) alicyclic diamines wherein at least one amino moiety is primary or secondary provided no more than one amino moiety is primary;
   (B) aliphatic polyamines containing at least three amino moieties wherein at least one is primary or secondary; and
   (C) aliphatic amino ethers containing at least one ether linkage and at least one amino moiety which is primary or secondary.

3. The process of claim 1 wherein the organic amine is an aliphatic polyamine containing at least three amino moieties wherein at least one is primary or secondary.

4. The process of claim 1 wherein the organic amine is diethylenetriamine.

5. The process of claim 1 wherein the impregnating solution contains from about 12 to about 25 weight percent silver.

6. The process of claim 1 wherein the silver salt in the said impregnating solution is a silver salt of an organic acid selected from the group consisting of monocarboxylic acids, dicarboxylic acids and mixtures thereof and wherein the organic moiety in the said acids contains less than 10 carbon atoms.

7. The process of claim 1 wherein the silver salt in the said impregnating solution is selected from the group consisting of silver carbonate, silver acetate, silver malonate, silver glycolate, silver oxalate, silver formate, silver citrate, silver lactate and silver pyruvate.

8. The process of claim 1 wherein in the said impregnating solution the solvent is water.

9. The process of claim 1 wherein the perchlorate salt in the impregnating solution is cesium perchlorate.

10. The process of claim 1 wherein the said perchlorate salt in the impregnating solution is rubidium perchlorate.

11. The process of claim 1 wherein the said impregnating solution contains from about 0.5 to about 8 milliequivalent weights of the perhalogenated acid per milliequivalent weight of the perchlorate salt.

12. The process of claim 1 wherein the said perchlorate salt in the impregnating solution is cesium perchlorate and the impregnating solution contains about 0.5 to about 8 milliequivalent weights of perchloric acid per milliequivalent weight of cesium perchlorate.

13. The process of claim 1 wherein in the said impregnating solution the silver salt is silver oxalate, the organic amine is diethylenetriamine and the perchlorate salt is cesium perchlorate.

14. The process of claim 1 wherein in the said impregnating solution the silver salt is silver oxalate, the organic amine is diethylenetriamine and the perchlorate salt is rubidium perchlorate.

15. The process of claim 13 wherein the said impregnating solution also contains from about 0.5 to about 8 milliequivalent weights of perchloric acid per milliequivalent weight of cesium perchlorate.

16. The process of claim 14 wherein the said impregnating solution also contains from about 0.5 to about 8 milliequivalent weights of perchloric acid per milliequivalent weight of rubidium perchlorate.

17. The process of claim 1 wherein the said impregnating solution contains about 10 to about 800 ppm of the cesium or rubidium cation.

18. A solution for impregnating a porous inorganic catalyst support comprising:

(a) a silver salt sufficient to produce a concentration of silver in the solution of from about 12 to about 25 weight percent,
(b) an organic amine solubilizing/reducing agent,
(c) a perchlorate salt of a higher alkali metal selected from the group consisting of cesium, rubidium and mixtures thereof sufficient to produce a concentration of the higher alkali metal in the solution of from 10 to about 800 ppm,
(d) an aqueous solvent, and
(e) a perhalogenated acid selected from the group consisting of perchloric acid, periodic acid, perbromic acid and mixtures thereof in an amount of from 0.5 to 20 milliequivalent weights per milliequivalent weight of the perchlorate salt in the said solution.

19. The solution of claim 18 wherein the said organic amine solubilizing/reducing agent is selected from the group consisting of:
   (A) alicyclic diamines wherein at least one amino moiety is primary or secondary provided no more than one amino moiety is primary;
   (B) aliphatic polyamines containing at least three amino moieties wherein at least one is primary or secondary; and
   (C) aliphatic amino ethers containing at least one ether linkage and at least one amino moiety which is primary or secondary.

20. The solution of claim 18 wherein in the said organic amine solubilizing/reducing agent is an aliphatic polyamine containing at least three amino moieties wherein at least one is primary or secondary.

21. The solution of claim 18 wherein the organic amine is diethylenetriamine.

22. The solution of claim 18 wherein the silver salt in the said impregnating solution is a silver salt of an organic acid selected from the group consisting of monocarboxylic acids, dicarboxylic acids and mixtures thereof and wherein the organic moiety in the said acids contains less than 10 carbon atoms.

23. The solution of claim 18 wherein the silver salt in the said impregnating solution is selected from the group consisting of silver carbonate, silver acetate, silver malonate, silver glycolate, silver oxalate, silver formate, silver citrate, silver lactate and silver pyruvate.

24. The solution of claim 18 wherein in the said impregnating solution the solvent is water.

25. The solution of claim 18 wherein the perchlorate salt in the impregnating solution is cesium perchlorate.

26. The solution of claim 18 wherein the said perchlorate salt in the impregnating solution is rubidium perchlorate.

* * * * *